US00PP31677P2

(12) United States Plant Patent
Hansen

(10) Patent No.: US PP31,677 P2
(45) Date of Patent: Apr. 14, 2020

(54) ***HEUCHERA* PLANT NAMED 'TIMELESS GLOW'**

(50) Latin Name: ***Heuchera* hybrid**
Varietal Denomination: Timeless Glow

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,865

(22) Filed: Jan. 24, 2019

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 5/025; A01H 6/80; A01H 6/00
See application file for complete search history.

(56) References Cited

PUBLICATIONS

Germania Seed Walters Gardens Bare Root and Plug Perennials 2019, retrieved on Oct. 1, 2019, retrieved from the Internet at https://www.germaniaseed.com/pdf/2019/749_walters.pdf, pp. 1,13,24. (Year: 2019).*

Park Seed Walter's Gardens 2019, retrieved on Oct. 1, 2019, retrieved from the Internet at https://parkseed.com/images/ART/WALTERS%202019.pdf, 2 pages total. (Year: 2019).*

* cited by examiner

*Primary Examiner* — June Hwu

(57) ABSTRACT

The new and distinct hybrid of *Heuchera* plant named 'Timeless Glow' with many small-sized foliage with rounded apices and lobes. Tightly-branched, upright, wine-colored panicles are repeatedly produced from early summer to early fall for at least fourteen weeks displaying large, rosy-pink flowers. The new plant has a compact habit, is vigorous and produces showy, long-flowering, herbaceous, perennial mounds of leaves beginning the season chartreuse-yellow and developing a silver overlay between the veins, and a dark red region surrounding the veins. The new plants is effective as a specimen plant, en masse, or as a container plant in the landscape.

1 Drawing Sheet

Botanical denomination: *Heuchera* hybrid.
Variety denomination: 'Timeless Glow'.

STATEMENT REGARDING PRIOR DISCLOSURES UNDER 37 CFR 1.77(B)(6)

The first public disclosure of the claimed plant, in the form of a website to the public and email release to customers, was made by Walters Gardens, Inc. on Feb. 1, 2018 followed by the Walters Gardens, Inc. Summer 2018-Spring 2019 catalog. The first public sales of *Heuchera* 'Timeless Glow' was by Walters Gardens, Inc. on Jul. 9, 2018. Walters Gardens, Inc. obtained the new plant and information about the new plant directly from the inventor. No plants of *Heuchera* 'Timeless Glow' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of *Heuchera* 'Timeless Glow'. 'Timeless Glow' was hybridized by the inventor on Jan. 28, 2015 at a wholesale perennial nursery in Zeeland, Mich., USA. The seed or female parent was 'Berry Timeless' U.S. Plant Pat. No. 26,357 and the pollen or male parent was 'Cherry Cola' U.S. Plant Pat. No. 22,967.

*Heuchera* 'Timeless Glow' was first selected in the fall of 2016 and passed final evaluation in the fall of 2017 from among many other seedlings from the same cross and hundreds of other crosses and assigned the breeder code 15-16-2 through the remaining evaluation process. *Heuchera* 'Timeless Glow' has been asexually propagated initially by basal cuttings at the same nursery in Zeeland, Mich. in 2016 and later by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: the female parent 'Berry Timeless', 'Sweet Tart' U.S. Plant Pat. No. 24,573, 'Blondie' U.S. Plant Pat. No. 24,564 and 'Appletini' U.S. Plant Pat. No. 29,396. 'Berry Timeless' has smaller flowers and the foliage is more chartreuse-yellow in the earlier part of the season. 'Sweet Tart' has a similar profusion of flowers throughout the season but the flower color is lighter pink and the foliage is light green with slight silvering between the veins. 'Blondie' has caramel-colored foliage with bronze and the flowers are creamy-yellow. 'Appletini' has larger lime-green foliage with silver between the veins and bright red flowers with only occasional rebloom. The male parent, 'Cherry Cola', has reddish-brown foliage and the flowers are produced over a shorter period. *Heuchera* 'Timeless Glow' differs from its parents as well as all other coral bells known to the applicant in the following combined traits:

1. The small, flat, glossy foliage has rounded apices and lobes.
2. Leaf blades emerge chartreuse-yellow and develop a silver overlay between the area surrounding the veins.
3. Leaf blades are moderately dissected with apices broadly rounded and mucronulate.
4. Flowers are outwardly-facing to slightly drooping, rosy-pink on wine-colored stems.
5. Flowering period begins in early summer and continues for at least fourteen weeks into early fall with repeat panicles.
6. Compact, dense, heavily-branched panicles display flowers at multiple nodes beginning just under foliage.
7. The new plant is vigorous and produces compact clumps and many small to medium-sized individual leaves.

BRIEF DESCRIPTION OF THE DRAWINGS

The photographs of *Heuchera* 'Timeless Glow' demonstrate the overall appearance of the plant including the unique traits of a plant in a partially-shaded greenhouse in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
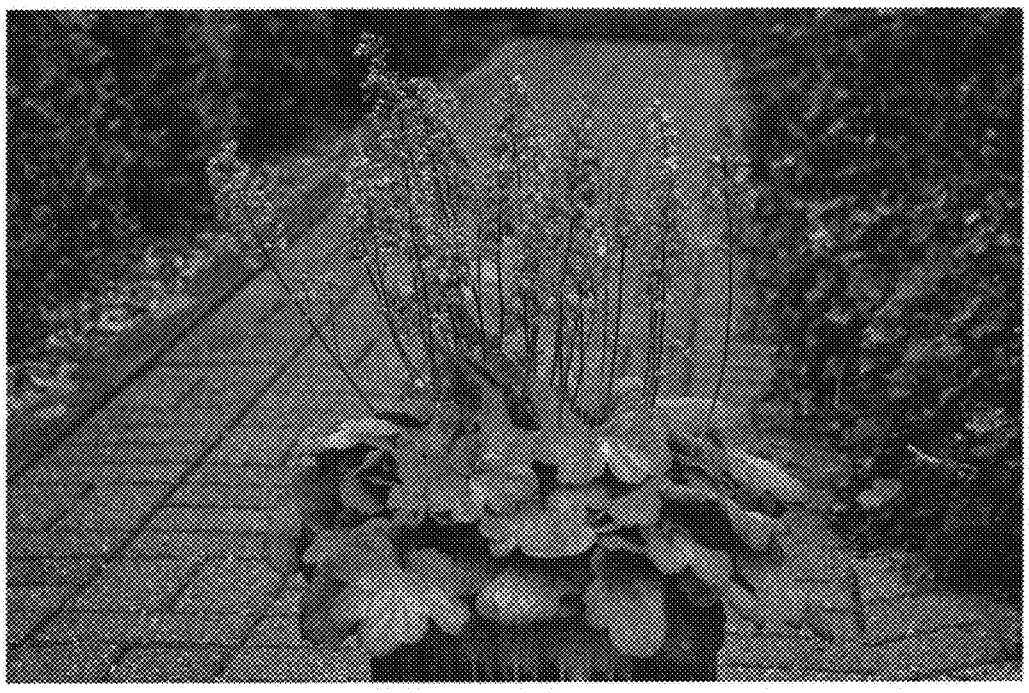
FIG. 1 shows a two-year-old plant grown in a container in a partially shaded greenhouse in peak flowering season.
Figure 2:
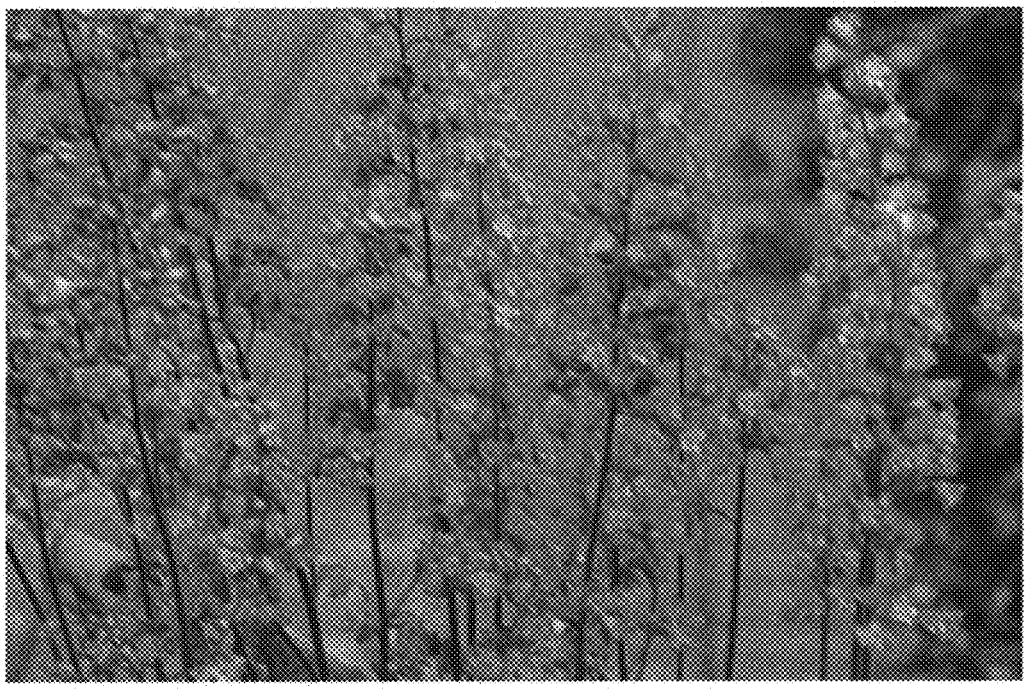
FIG. 2 shows a close-up of flower panicles with buds and flowers from a two-year-old plant.

The following description is based on two-year-old plants growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Berry Timeless'; the male or pollen parent was 'Cherry Cola';

Plant habit: Hardy herbaceous perennial with basal rosette of foliage; mounded foliage to about 14.0 cm tall and 45.0 cm in diameter with scapes to about 48.0 cm long; with about 14 stems per plant to about 5.0 cm long and 1.2 cm diameter at base, with about 25 to 30 leaves per stem; about 5 panicles per stem flowering at one time;

Roots: Fibrous, finely branched;

Growth rate: Rapid, rooting from basal cuttings in two weeks and finishing in three-liter container in about two and a half months;

Foliage: Cordate to deltoid; micro-puberulent adaxial and abaxial; palmately moderately lobed with five main distinctly dissected lobes, dissected about one-third the distance to the petiole; with few, typically four shallow indentations; apex and lobe apices rounded and mucronulate; base cordate with basal lobes typically not overlapping; margins crenate to mucronulate, ciliolate; surface matte adaxial and abaxial; held nearly horizontal; margin mostly flat;

Leaf blade size: To about 11.0 cm wide and 10.0 cm long, average about 9.5 cm wide and 9.5 cm long;

Leaf color: Spring and young emerging adaxial nearest RHS 145A distally and RHS 144A proximally between veins, and area surrounding veins blend between RHS 183B and RHS 187B; spring young emerging abaxial lighter than RHS 146D between veins and surrounding veins nearest RHS 187C; mature mid-season adaxial nearest blend between RHS 146B and RHS 138A along perimeter 1.0 cm, with silver between RHS 193A and RHS 192A between veins toward center; and nearest RHS 183A in the 1.0 to 2.0 mm surrounding the main veins and nearest RHS 138A surrounding smaller veins; mature mid-season abaxial between RHS 146D and RHS 145A with blush nearest RHS 183A concentrated around main veins; fall and winter adaxial perimeter nearest RHS 138A and central portions, with RHS 194D portion surrounding veins toward center portion and nearest RHS 183A surrounding some of the major veins; abaxial fall and winter nearest RHS 148C with undertone of nearest RHS 183B;

Leaf quantity: Dense, about 300 per plant;

Veins: Palmate; sparsely hirsutulous and costate abaxial, glabrous and nearly flat adaxial;

Vein color: Emerging or early spring adaxial nearest RHS 11C and abaxial nearest RHS 145D; mid flowering season main adaxial lighter than RHS 146D and smaller secondary veins nearest RHS 145A, mid flowering season abaxial nearest RHS 145C; late season adaxial variable, nearest RHS 145D proximally, transitioning to nearest RHS 138B along perimeter and nearest RHS 138A in the middle; abaxial RHS 145D;

Petiole: Cylindrical, base amplexicaul; sparsely pubescent with hairs to about 1.0 mm long; to about 14.0 cm long and 3.0 mm wide above stipule; average about 12.0 cm long and about 2.5 mm diameter above stipule;

Petiole color: Emerging leaf nearest RHS 146D; flowering season mature leaf nearest RHS 146D; late season nearest RHS 146C;

Stipule: Flared at base of petiole; glaucous abaxial and adaxial; margin ciliate; to about 12.0 mm long and about 10.0 mm wide at base; with two lateral projections of about 7.0 mm long and 1.5 mm across in distal portion;

Stipule color: Young expanding through mature late season adaxial and abaxial nearest RHS 145D toward center and nearest RHS 155D along margins;

Peduncle: Panicle; cylindrical; stiff; pubescent; upright; densely compound branched; to about 48.0 cm long and 3.5 mm diameter at base, average about 44.0 cm tall and 3.0 mm diameter; about 36 peduncles per plant at one time; up to about 600 flowers per panicle, average about 300; initial flowers under foliage; tightly-branched panicle with up to 20 branches up to 11.0 cm long and 1.0 mm diameter decreasing distally, average 18 branches per panicle; branches mostly upright to about 70° to 80° above horizontal; branches subtended by single foliar bract; flower density high;

Peduncle color: Nearest RHS 183A distally and lighter than RHS 146D below foliage;

Foliar bract: Oblong palmate; incised margins to deeply lobed; apex acute and lobes; truncate clasping base; to 1.4 cm long and 9.0 mm across, decreasing distally; sessile;

Foliar bract color: Adaxial and abaxial nearest RHS 146D distally with slight blush of nearest RHS 183B proximally;

Flowering longevity: Panicle effective for about two to four weeks; individual flowers about 5 days; self-cleaning;

Flowering period: Beginning early summer and repeating with new panicles without the need to remove old panicles through early fall for at least 14 weeks;

Pedicel: Cylindrical; puberulent; to about 3.0 mm long and 0.5 mm diameter, average about 2.0 mm long and 0.5 mm diameter; attitude outwardly;

Pedicel color: Nearest RHS 183A;

Buds one day prior to opening: Ellipsoidal; rounded apex and attenuate base; puberulent to glandular; about 5.0 mm long and 3.0 mm diameter;

Bud color one day prior to opening: Nearest RHS 60A;

Flower: Perfect; campanulate; actinomorphic; about 8.0 mm long and 8.0 mm in diameter at corolla face;

Flower attitude: Outwardly;

Calyx: Base fused to form hypanthium; puberulent to glandular abaxial, glabrous adaxial; about 8.0 mm long and 8.0 mm wide at apex;

Sepals: Five; lanceolate; acute apex, fused in basal 4.0 mm; to about 8.0 mm long and 3.0 mm wide at fusion;

Sepal color: Abaxial nearest RHS 60A, adaxial nearest RHS 60A;

Petals: Five; oblanceolate to spatulate; subacute apex and attenuate base; margin entire; glabrous adaxial and abaxial; about 4.0 mm long and 1.0 mm wide in middle;

Petal color: Abaxial nearest RHS 73D and adaxial between RHS 63C and RHS 63B;

Androecium: Five; adaxial to sepal about 1.0 mm above base;

*Filaments*.—Five, thin, glabrous; about 2.0 mm long and about 0.3 mm diameter; color nearest RHS NN155B.

*Anthers*.—Ellipsoidal, distinct, basifixed, longitudinal; about 1.0 mm long and about 0.5 mm across; color nearest RHS 18C.

*Pollen*.—Has not been observed.

Gynoecium: One, two-beaked; half-inferior; bifid style with pistil split at ovary; about 6.0 mm long;

*Style*.—Bifid; split apart at apex of ovary; about 3.0 mm long and about 0.5 mm diameter; color nearest RHS 160C.

*Stigma*.—Acute apex, about 0.3 mm diameter; color nearest RHS 157A.

*Ovary*.—Half-inferior, about 3.0 mm long and 2.0 mm diameter; ellipsoidal to globose; acute apex and base rounded; color lighter than RHS 160B.

Fruit: not yet observed;

Seeds: not yet observed;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct coral bells plant named *Heuchera* 'Timeless Glow' as herein described and illustrated.

* * * * *